United States Patent [19]

Evans et al.

[11] Patent Number: 4,697,465

[45] Date of Patent: Oct. 6, 1987

[54] TEST COUPON HOLDER

[76] Inventors: Willie V. Evans, 104 W. Lantrip; Gary K. Evans, 707 Danville Rd., both of Kilgore, Tex. 75662

[21] Appl. No.: 855,707

[22] Filed: Apr. 25, 1986

[51] Int. Cl.[4] .......................... G01N 3/00; G01N 17/00
[52] U.S. Cl. ................................... 73/866.5; 422/53; 436/6; 73/86
[58] Field of Search .................. 422/53; 73/86, 866.5; 436/6

[56] References Cited

U.S. PATENT DOCUMENTS

| | | |
|---|---|---|
| 1,769,463 | 7/1930 | Rice . |
| 2,679,752 | 6/1954 | Metler . |
| 2,752,228 | 6/1956 | Gould . |
| 2,763,534 | 9/1956 | Campbell ........................... 422/53 |
| 2,770,532 | 11/1956 | Mason ................................. 422/53 |
| 2,870,629 | 1/1959 | Willis . |
| 3,174,332 | 3/1965 | Echtler, Jr. et al. . |
| 3,718,034 | 2/1973 | Swearingen ......................... 73/86 |
| 3,948,744 | 4/1976 | Cushing . |
| 4,002,059 | 1/1977 | Jeffers et al. . |
| 4,120,313 | 10/1978 | Lewis . |
| 4,177,676 | 12/1979 | Welker .............................. 73/866.5 |
| 4,179,920 | 12/1979 | Schuller et al. . |
| 4,275,592 | 6/1981 | Atwood et al. . |
| 4,309,899 | 1/1982 | Torres ................................. 73/86 |

Primary Examiner—David L. Lacey
Assistant Examiner—Floyd E. Bennett, Jr.
Attorney, Agent, or Firm—Banner, Birch, McKie & Beckett

[57] ABSTRACT

A corrosion coupon holder for inserting and removing a coupon from the interior of a pipeline while under pressure has an elongated housing with a threaded connection at one end and a removable closure device at the other end, the housing connection to be attached to a pipe entry valve which is connected as a branch to the pipeline. The housing other end also carries a guide body having a bore which guidingly and sealingly receives a rod for inserting a coupon having a safety stop element at one end to hold the coupon, the guide body having a split collet associated with the bore with a locking screw mounted to act on the collet to fixedly clamp the rod in the bore of the guide body and the housing having a bleeder valve communicating with the interior to relieve pressure from within such interior.

4 Claims, 2 Drawing Figures

TEST COUPON HOLDER

BACKGROUND OF THE INVENTION

This invention relates generally to pipeline corrosion detecting devices for measurement of the corrosive effect of fluid whether gas or liquid carried in the pipeline. More particularly, the invention relates to test coupon holders for inserting and retrieving coupons from large diameter pipelines to periodically check for corrosion and wear of the pipeline due to flow of a medium such as corrosive fluids or suspensions through the pipeline.

It has become customary to determine the corrosiveness of a pipeline fluid in order to estimate the extent of corrosion to the interior surfaces of the pipeline by inserting into the flowing fluid a coupon of metal of standardized size, shape, composition and finish. By visual inspection or by measuring the loss of weight for a selected period of immersion in the fluid, the rate of corrosion can be determined. Frequently the coupons are inserted into the pipeline while the line is shut down by removing a plug from the pipeline, inserting the coupon and then replacing the plug so as to seal the line against leakage.

It is known that the flow of fluids or suspensions through pipelines can result in corrosion and deterioration of the pipeline at its inner wall. Such pipelines may often be inaccessible due to being buried under ground or otherwise concealed. Thus inserting test coupons constructed of a suitable material such as the material of the pipeline itself for establishing the corrosive effects on the coupon, the corrosive effects are in turn indicative of similar effects on the pipeline.

However, in many situations it is impractical to shut down the pipeline and relieve the pressure within the pipeline each time it is desired to insert or remove a coupon. Thus, the prior art has developed devices by which test coupons may be inserted into the pipeline while the fluid flowing through the line is under pressure within the line. The coupon so positioned may remain within the line for predetermined periods of time and then be removed from the line without interrupting the fluid flow under pressure through the line.

A primary object of this invention is to provide a device for inserting into and retrieving a corrosion test coupon from the interior of a pipeline while the pipeline is operating with fluid flow under pressure.

It is another object of this invention to provide a device for positioning a corrosion test coupon inside a pipeline while the pipeline is under fluid pressure with complete safety to the operator of the device in inserting or retrieving the coupon.

It is a still further object of this invention to provide a test coupon holder having a coupon inserting rod provided with a safety stop element to prevent inadvertent withdrawal of the coupon inserting rod from the holder.

Another object of this invention is to provide a test coupon holder having a rod reciprocable in an elongated housing with the rod carrying the coupon and clamping means being provided in association with the housing to clamp the rod at desired locations to obtain proper positioning of the coupon within the pipeline being tested.

SUMMARY OF THE INVENTION

The above and other objects are realized and the limitations of the prior art are overcome by providing a branch to the pipeline with a pipe entry valve disposed in such branch. An elongated cylindrical housing is attached to the valve with the housing having a guide body provided with a bore in communication with the chamber within the elongated housing. The bore guidingly and sealingly receives a rod to be reciprocated within the housing chamber, the rod having a safety stop element fixedly secured to one end thereof. This element is provided with means to releaseably hold the coupon.

The guide body of the elongated housing has a collet means associated with the bore and a locking means carried by the guide body accessible from the exterior of the body to be operable to engage the collet means and thereby fixedly clamp the rod in the bore at selected desired locations to obtain the desired positioning of the coupon within the pipeline.

BRIEF DESCRIPTION OF THE DRAWINGS

The above mentioned and other objects and advantages of this invention and a better understanding of the principles and details of the invention will be evident from the following description taken in conjunction with the appended drawing.

DESCRIPTION OF THE PREFERRED EMBODIMENT

Figure 1:
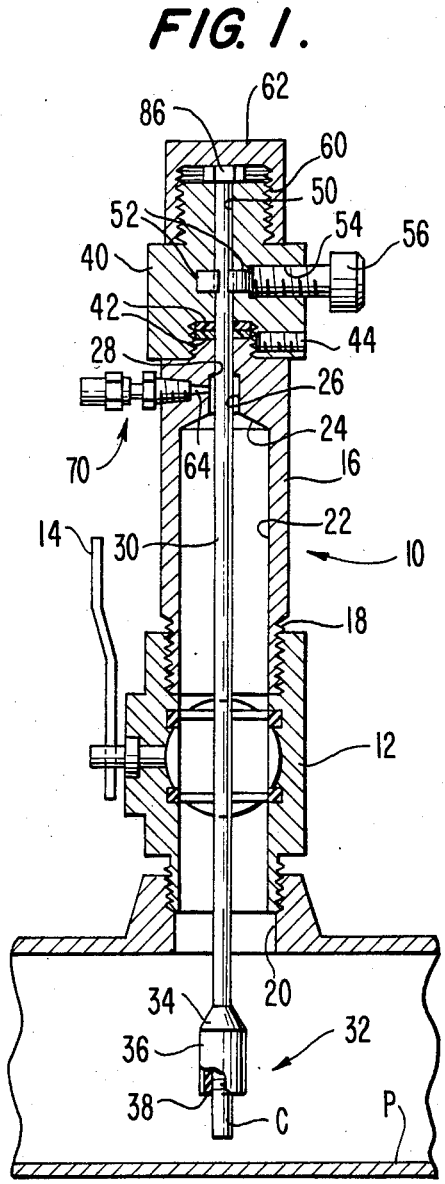
FIG. 1 is a sectional view of the test coupon holder of this invention associated with a pipe entry valve and a segment of pipeline, the test coupon being in position within the pipeline.

Referring to the drawing, the test coupon holder 10 of this invention is shown mounted on a section of pipeline P that is to be tested by means of a pipe entry valve 12. Valve 12 is thus connected as a branch to the pipeline section P. Valve 12 is of a type which has a clear passage, such as a ball valve or plug valve, so that by a 90° turn applied to valve 12 by means of the operating handle 14, the valve can be changed from open to closed to thereby place the test coupon holder 10 either in communication with the interior of pipeline section P or isolate the holder 10 from the pressure within pipeline section P.

The holder 10 has an elongated housing 16 provided at one end thereof with threads 18, these threads engaging with the internal threads on pipe entry valve 12 to thereby mount the test coupon holder 10 on valve 12 which in turn is threaded into an opening 20 leading to the interior of pipe section P. Housing 16 provides an internal elongated chamber 22 which in the mounted relationship shown on FIG. 1 is in alignment with the clear open passage of pipe entry valve 12 leading into the interior of pipe section P.

The end of housing 16 opposite threads 18 is provided with an end wall 24 which is conical in configuration and leads to a central aperture 26. Aperture 26 extending axially from the elongated cylindrical housing 16 has two separate diameter portions the smaller diameter portion 28 snuggly and slideably receiving a test rod 30. Rod 30 extends axially through chamber 22 of housing 16 and, as shown in section on FIG. 1, with pipe entry valve 12 open, the rod projects through the valve and down into the interior of pipe section P. The end of rod 30 has a safety stop element 32 fixedly secured thereto as by having the rod end threaded and element 32 having a female threaded portion (not shown) threaded onto the end of rod 30.

Safety stop element 32 has a generally conical portion 34 leading to its connection with rod 30. The element 32 is provided with a hollow cylindrical metallic casing 36, this casing being filled with an insulating material 38 such as a phenolic material. The insulating material is centrally drilled and tapped. This tapped bore in the insulating material forms the holder for the coupon C, the coupon simply being threaded at one end and screwed into the threaded bore within insulating material 38. This construction for the stop element 32 assures that the hollow metallic casing 36 protects the insulating material 38 whereas the coupon is positioned to extend freely away from the end of element 32 and rod 30. Insulating coupon C, isolated from the other metal parts of holder 10, valve 12 and pipe section P, avoids undesired electrolytic action involving coupon C.

The upper end of housing 16 above end wall 24, aperture 26 and small aperture portion 28 is threaded to receive a guide body 40 which is threaded onto the end of housing 16. A pair of annular seals 42 which may be of teflon are disposed between the threadably engaged portions of housing 16 and guide body 40. These annular seals 42 surround the rod 30 after the rod passes through the small aperture portion 28 in the end wall 24 of housing 16. A set screw 44 is shown on FIG. 1 as threaded into a bore in guide body 40 to fixedly secure the body 40 onto the end of housing 16 securedly clamping the seals 42 between body 40 and housing 16.

The guide body 40 guidingly and sealingly receives the rod 30 within a bore 50 extending through guide body 40. Intermediate the ends of bore 50 there is provided a cavity which houses a split collet 52 with the two halves of the split collet being disposed on opposite sides of the bore 50, respectively.

A threaded bore 54 leading to the cavity that houses the split collet 52 contains a locking screw 56. Thus, when locking screw 56 is threaded into bore 54 until it engages with one half of the split collet 52, pressing that half against the opposite half of the collet, the rod 30 becomes firmly clamped with respect to the guide body 40 by the split collet 52 so it is unable to be expelled from the test coupon holder 10 under pipeline pressure within pipe section P, this same pressure existing within the chamber 22 of housing 16 when the pipe entry valve 12 is open.

By backing off on the locking screw 56, the split collet 52 releases its clamping relationship on rod 30 such that the rod may be withdrawn. Also the release of the split collet 52 by unscrewing locking screw 56 enables the axial position of the rod 30 and therefore the location of the coupon C within the pipe section P to be adjusted. Then the split collet 52 is reclamped by tightening down on the locking screw 56. This capability for the test coupon holder 10 is advantageous in that it enables locating the coupon C at the desired position within the pipe section P enabling the coupon holder 10 to be employed with pipelines of different diameter. Thus, the clamping means provided by the split collet 52 and locking screw 56 provides the coupon holder 10 with added versatility with respect to the areas of use.

The upper end of guide body 40 surrounding bore 50 is externally threaded at 60. In the installation shown on FIG. 1 where the coupon holder 10 is operatively associated with the open pipe entry valve 12 and pipe section P to specifically locate the coupon C in the pipe section, the length of rod 30 is such that the upper enlarged end of rod 30 is located down against the upper end of guide body 40 where bore 50 ends. In this condition while the coupon is undergoing testing with respect to the corrosive conditions which the pipe section P is undergoing by reason of fluid material flow through the pipe, an internally threaded cap 62 may be threaded onto threads 60 on guide body 40. This cap 62 acts to positively hold the rod 30 and coupon C in the desired predetermined position during the time period that the coupon C is being exposed to testing the corrosive conditions.

When the time period for the corrosive condition test has been completed, the operator need merely remove the cap 62, threading it off of threads 60 of body 40. The presence of cap 62 avoids any danger of rod 30 being expelled from the coupon holder 10 by pressure existing within chamber 22 of housing 16. This feature becomes particularly important should someone tamper with and thereby release the split collet 52 by unscrewing locking screw 56. Such a release of split collet 52 to free rod 30 without the presence of cap 62 could result in rod 30 being rapidly expelled from the coupon holder under the pipeline pressure.

It should also be pointed out that the construction of safety stop element 32 affixed to the end of rod 30 offers the coupon holder 10 added safety should cap 62 not be present and the split collet 52 become released. In such event, while the rod 30 would be rapidly expelled from the holder 10 under the pipeline pressure, the rod 30 would not be totally ejected from the coupon holder 10. Instead, the conical portion 34 of safety stop element 32 would pass through chamber 22 in housing 16 and engage against the apertured end wall 24 of housing 16 thereby preventing further expulsin of rod 30 with cap 62 removed and split collet 52 released.

The elongated cylindrical housing 16 is provided with a passageway 64 leading from aperture 26 which communicates with chamber 22 to the exterior of housing 16. The outer portion of passageway 64 is internally threaded and a bleeder valve 70 is then threaded into passageway 64. This bleeder valve may be of conventional construction. The valve enables the pressure in chamber 22 of housing 16 to be relieved when the operation of removing coupon C following termination of the corrosive testing is to be carried out. A typical type bleeder valve 70 would act to close off passageway 64 when the cap portion on the valve is threaded down onto the base portion and open passageway 64 when this cap portion is unscrewed to open the bleeder valve passage.

Figure 2:
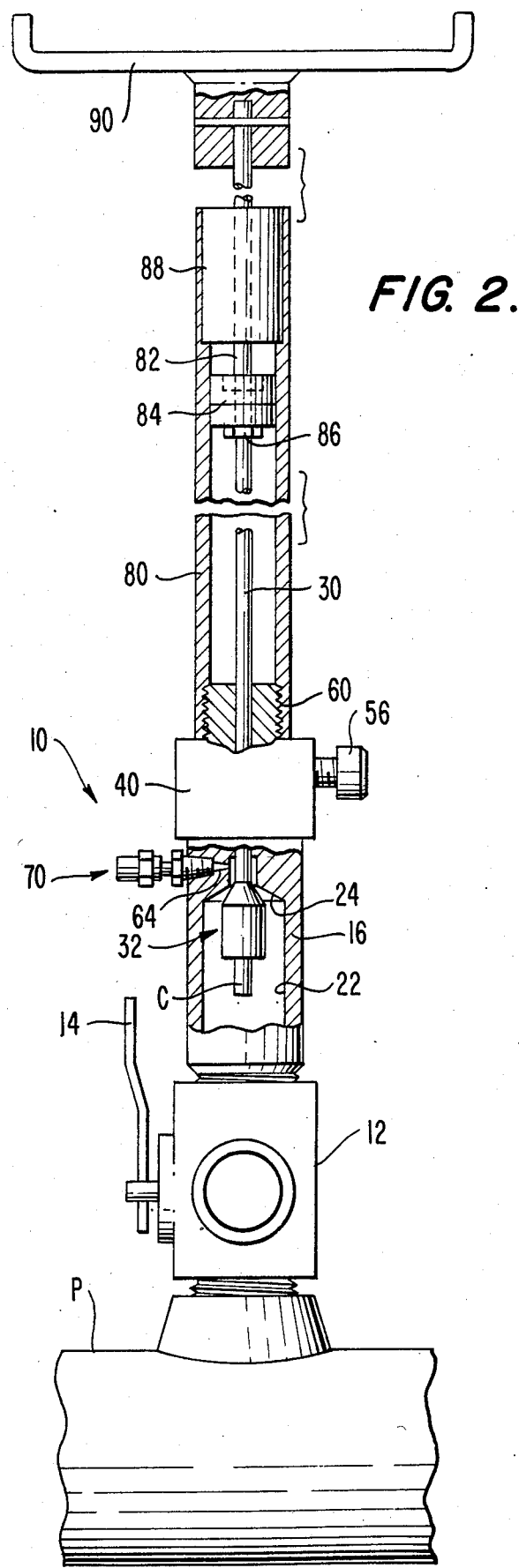
FIG. 2 is a partial sectional view showing the coupon withdrawn into the coupon holder housing.

As has been previously explained, the test coupon holder 10 is shown in FIG. 1 in its operative position in relative to pipe entry valve 12 and pipe section P while the coupon C is undertaking the corrosive testing process. In contrast, FIG. 2 shows the coupon holder 10 in the condition where the coupon C is either in readiness to be introduced into the pipe section P or has been retrieved from the pipe section P following undergoing the corrosive testing of the fluid within pipe section P.

The operation undertaken in removing the coupon C from the condition of the test coupon holder 10 shown in FIG. 1 following completion of a corrosive test may be described as follows: Initially cap 62 is removed thereby exposing the upper end of rod 30 on the exterior of guide body 40. Then an override housing 80 which has an internally threaded end is threaded onto the threads 60 on the outer end of guide body 40. The override housing 80 carries a retrieving rod 82. This retrieving rod carries a coupling 84 which mates with the upper end 86 of rod 30. This may be a threaded coupling between elements 84 and 86, a pin connection or other suitable interconnection made between the rod 30 and the retrieving rod 82. Such connecton forms no part of the invention herein.

The override housing 80 also carries a retrieving rod bushing 88 at its upper end which acts as a guide for the retrieving rod 82. The retrieving rod 82 has a handle 90 fixed to the outer end of the retrieving rod, this handle enabling the operator to manipulate rod 30 in carrying out the insertion and removal of coupon C from the interior of the pipeline section P.

Initially, in commencing to remove the coupon C from the pipeline section P after a corrosive test period has been concluded, the split collet 52 is released by unscrewing locking screw 56. This unclamps rod 30 with respect to guide body 40 and enables withdrawal of rod 30 carrying the test coupon C. However, careful control of releasing the split collet clamp 52 needs to be observed since the pipeline pressure acting on rod 30 tends to force the rod out of the coupon holder requiring control of this expelling action by firmly holding the handle 90 on the retrieving rod 82 which is coupled to rod 30.

With the retrieving rod 82 in place along with override housing 80, rod 30 is withdrawn thereby removing coupon C from within the pipe section P until it is disposed within chamber 22 of housing 16 as shown in FIG. 2.

Once the coupon C and safety stop element 32 on rod 30 have been withdrawn into the chamber 22 of housing 16, the pipe entry valve 12 is manipulated to its closed position thereby isolating the test coupon holder 10 from the pressure within the pipeline section P. With the pipeline pressure still existing within chamber 22, the bleeder valve 70 which has been in a closed position will be opened thereby bleeding the pressure from within chamber 22 through passageway 64 to the exterior.

Once the pressure within chamber 22 has been relieved, the entire test coupon holder 10 starting with housing 16 may be unthreaded where the threads 18 have been threaded into the body of pipe entry valve 12. With the coupon holder 10 now separated from pipe entry valve 12, the rod 30 may be manipulated as needed to expose the coupon C still carried by the safety stop element 32. Such exposure now occurs through the open end of chamber 22 in housing 16 where it has been disconnected from the pipe entry valve 12. Necessary inspection of the coupon C upon its removal from safety stop element 32 will now be carried out in determining the corrosive conditions existing within the pipeline section P.

Inserting a fresh coupon C for carrying out a further corrosive condition test essentially involves the reverse of the above described procedures. A new coupon C will be threaded into the insulator material 38 within the hollow metallic casing 36 of safety stop element 32 with this fresh coupon then being drawn up on rod 30 into the chamber 22 of housing 16. In this position such as shown on FIG. 2 the test coupon holder is in readiness to be reinstalled upon a pipe entry valve leading to the interior of a pipeline section P.

The bleeder valve 70 is closed and the threads 18 on housing 16 engaged with the internal threads of the pipe entry valve 12. At this stage the valve 12 is opened by manipulating handle 14 admitting the pipeline pressure into chamber 22 of housing 16 in the coupon holder 10. By reintroducing rod 30 down through chamber 22 and pipe entry valve 12, the new coupon C is introduced into the interior of pipeline section P. When rod 30 has been inserted to the desired extent to position coupon C at a predetermined position within pipeline section P the split collet 52 is tightened by screwing in locking screw 56 until the rod 30 is firmly clamped within the guide body 40 against possible displacing forces acting on the rod and coupon by reason of the pressure within the pipeline section P which pressure now exists within chamber 22 by reason of open pipe entry valve 12.

While the invention has been described with a certain degree of particularity, it is manifest that many changes may be made in the details of construction and the arrangement of components without departing from the sphere and scope of this disclosure. It is thus to be understood that the invention is not to be considered as limited to the embodiment set forth herein which has been set forth for purposes of exemplification only but is to be limited only by the scope of the attached claims, including the full range of equivalency to which each element thereof is entitled.

What is claimed is:

1. A test coupon holder for inserting and removing a coupon from the interior of a pipeline comprising:
    an elongated housing defining a chamber, said housing having connecting means at one end for connecting said housing to a pipe entry valve which is connected as a branch to a pipeline to be tested;
    a guide body mounted on the other end of said housing having a bore in communication with said chamber;
    a rod guidingly and sealingly received in said bore, said rod has a portion which extends through said housing and said portion has an end exterior of said housing for inserting a coupon;
    a safety stop element fixedly secured to said exterior end said element being provided with means to releasibly hold the coupon and including a hollow metallic casing having means at one end of said casing for connecting said element to said rod, said casing having an insulating material contained therein with said material being formed internally to provide said means to releasably hold the coupon;
    collet means positioned and arranged within said bore of said guide body to clamp said rod;
    locking means carried by said guide body and accessible from the exterior of said body to be operable to engage said collet means to fixedly clamp said rod in said bore; and
    bleeder valve means carried by said housing communicating with said chamber to relieve pressure within said chamber.

2. A test coupon holder as recited in claim 1 wherein said housing has an apertured end wall closing the other end of said housing, said rod passing through the aperture in said end wall, and said safety stop element being engageable with said end wall to prevent expelling said rod under pipeline pressure existing within said chamber.

3. A test coupon holder as recited in claim 1 wherein said collet means includes a split collet having the halves thereof disposed on opposite sides of said bore respectively, and said locking means comprises a locking screw threaded into said guide body and directed toward said bore.

4. A test coupon holder as recited in claim 1 wherein the outer end of said guide body includes attaching means, and said holder further includes closure cap means removably attached to said attaching means.

* * * * *